(12) United States Patent
Schätzl

(10) Patent No.: US 10,398,872 B2
(45) Date of Patent: *Sep. 3, 2019

(54) MOUTHPIECE FOR CONTROLLED DELIVERY OF A BREATHING GAS

(71) Applicant: ResMed R&D Germany GmbH, Martinsried (DE)

(72) Inventor: Stefan Thomas Schätzl, Schwifting (DE)

(73) Assignee: ResMed R&D Germany GmbH, Martinsried (DE)

( * ) Notice: Subject to any disclaimer, the term of this patent is extended or adjusted under 35 U.S.C. 154(b) by 470 days.

This patent is subject to a terminal disclaimer.

(21) Appl. No.: 15/048,171

(22) Filed: Feb. 19, 2016

(65) Prior Publication Data

US 2016/0166798 A1 Jun. 16, 2016

Related U.S. Application Data

(63) Continuation of application No. 13/429,705, filed on Mar. 26, 2012, now Pat. No. 9,295,804.

(30) Foreign Application Priority Data

Mar. 29, 2011 (EP) .................................... 11160273

(51) Int. Cl.
*A61M 16/00* (2006.01)
*A61M 16/20* (2006.01)
(Continued)

(52) U.S. Cl.
CPC ...... *A61M 16/206* (2014.02); *A61M 16/0057* (2013.01); *A61M 16/049* (2014.02);
(Continued)

(58) Field of Classification Search
CPC ............ A61M 16/206; A61M 16/0875; A61M 16/201; A61M 16/049; A61M 16/0057;
(Continued)

(56) References Cited

U.S. PATENT DOCUMENTS 4,338,884 A 7/1982 Atchley et al.
5,868,130 A 2/1999 Stier
(Continued)

FOREIGN PATENT DOCUMENTS

EP 1 884 254 A1 2/2008

*Primary Examiner* — Steven O Douglas
(74) *Attorney, Agent, or Firm* — Nixon & Vanderhye P.C.

(57) ABSTRACT

A mouthpiece for controlled delivery of a breathing gas including oxygen, preferably an increased ratio of oxygen with respect to ambient air, to the respiratory tracts of a user which includes a valve having two modes: a closed default mode, which substantially impedes any flow of the breathing gas through the valve; and an active open mode, which allows for a substantial flow of the breathing gas through the valve, wherein the open mode can be activated by the user manipulating the valve with his/her mouth. Such a valve may be used in a device for delivery of breathing gas and in an apparatus for controlled delivery of the breathing gas to the respiratory tracts of a user. A method for controlled delivery of the breathing gas to the respiratory tracts of a user may include operating the valve.

20 Claims, 2 Drawing Sheets

(51) Int. Cl.
*A61M 16/04* (2006.01)
*A62B 9/06* (2006.01)
*A61M 16/08* (2006.01)

(52) U.S. Cl.
CPC .... *A61M 16/0488* (2013.01); *A61M 16/0875* (2013.01); *A61M 16/20* (2013.01); *A61M 16/201* (2014.02); *A62B 9/06* (2013.01); *A61M 2210/0625* (2013.01); *A61M 2210/0637* (2013.01); *A61M 2210/0643* (2013.01)

(58) Field of Classification Search
CPC .............. A61M 16/0488; A61M 16/20; A61M 2210/0643; A61M 2210/0625; A62B 9/06
USPC ............ 128/201.28, 204.26, 205.24, 206.29; 251/364
See application file for complete search history.

(56) References Cited

U.S. PATENT DOCUMENTS

| | | | |
|---|---|---|---|
| 7,267,245 | B2 | 9/2007 | Yang |
| 9,295,804 | B2 * | 3/2016 | Schatzl ............. A61M 16/0488 |
| 2005/0242130 | A1 | 11/2005 | Yang |
| 2009/0302261 | A1 | 12/2009 | Skillern |

\* cited by examiner

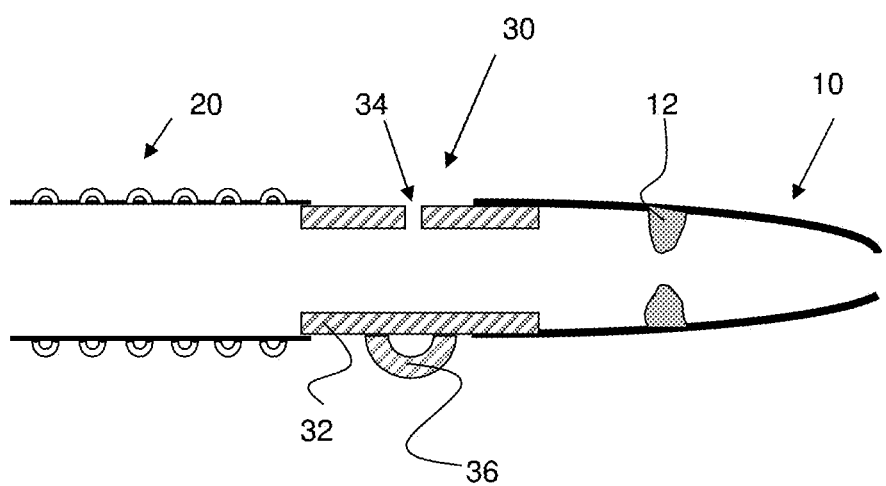

MOUTHPIECE FOR CONTROLLED DELIVERY OF A BREATHING GAS

This application is a continuation of U.S. patent application Ser. No. 13/429,705, filed Mar. 26, 2012, which claims priority to European Patent Application No. EP 11 16 0273.6, filed Mar. 29, 2011, the contents of each of which are incorporated herein by reference in its entirety.

TECHNICAL FIELD

The present invention generally refers to a device, a method, an apparatus and a use of said device for delivery of a breathing gas to a user.

BACKGROUND OF THE INVENTION

Patients with, particularly pulmonary, diseases often need an additional supply of oxygen. Commonly, this is achieved by numerous devices. The basic working principle of these devices is that an end of a tube is placed in the respiratory tracts of the patient. This end may be placed in the patient's mouth, in the patient's wind-pipe or in the patient's lung. In the last two cases the tube may generally enter the patient's body via his/her mouth or via his/her nose. Once the end is placed in the patient's respiratory tracts, a generally constant flow of a breathing gas including oxygen is supplied through the tube. By this, the patient is supplied with additional oxygen.

However, the existing systems have certain major drawbacks and problems limiting their usability. As the flow of breathing gas is generally constant, the device is constantly open—that is, gas can flow. This has numerous undesired effects, some of which are discussed below. When the patient using such a device exhales, part of the exhaled "used" air may enter the tube. This is undesired for different reasons. First, the patient may inhale this used air in the following breath, making the method less effective. Second, the exhaled air may cause noise when reentering the tube of the device. Third, this may trigger leak alarms. Fourth, such constant flow may be inconvenient for the patient. Another undesired effect is the fact that part of the breathing gas is wasted—that is, not used efficiently by the patient; when the breathing gas continuously enters the respiratory tracts of the user, it also enters his/her respiratory tracts when the user does not breath in or even when the user exhales. The breathing gas being released during these times cannot be used efficiently by the patient. This is undesirable for different reasons. First, wasting the breathing gas is not economical since more breathing gas is released than used. This leads to costs which are higher than what would be necessary. The second reason relates to the use of oxygen in mobile units and/or at home. In both cases the user generally has to make use of breathing gas tanks or bottles—in the one case at home, in the other case one can think of a user having a moveable or portable device (e.g. with wheels such as a trolley-like device) where the gas tank can be placed upon, allowing the user to leave his/her room of home. If the breathing gas is not used efficiently, the gas tank has to be larger than necessary (to allow for the same duration of gas flow) or needs to be changed more often. Both alternatives are inconvenient for the user.

To summarize, the current state of the art does not use the breathing gas efficiently and has numerous undesired effects, including higher than necessary costs and numerous inconvenient aspects for the user.

EP 1 884 254 A1 relates to a valve balloon for inhalers having a valve mechanism for filling and emptying a valve balloon. Further EP 1 884 254 A1 discloses a mouthpiece and a membrane. To open the valve mechanism, the mouthpiece is pushed against the membrane in a direction being generally parallel to the gas flow, thereby bringing the mouthpiece into communication with an inner space of a balloon. However, pushing a mouthpiece against a membrane to open the membrane may require a certain force. If used continuously in a device for delivering breathing gas to a user, the user of such a device may indeed get tired to repeat performing this procedure and may leave the mouthpiece in permanent gas communication with the other devices. Further, pushing the mouthpiece against the membrane by applying a certain force may seem unnatural and not intuitive for a user. A device as disclosed in EP 1884 254 A1 is therefore not suitable to be used for additional supply of oxygen to a user for a prolonged period of time.

It is therefore an object of the current invention to provide a device, a method, an apparatus and a use of said device for delivery of a breathing gas to a user which overcome or at least ameliorate the mentioned disadvantages.

SUMMARY OF THE INVENTION

This object is achieved by the device, the method, the apparatus and the use according to the independent claims. Preferred embodiments of the present invention are discussed in the dependent claims.

According to one aspect, the present invention provides a mouthpiece. In the context of the present invention, a mouthpiece is particularly a device adapted to control the supply of breathing gas to the respiratory tracts of the user. Preferably, a mouthpiece is placed in the user's mouth when used. Preferably, a tube is used to bring the breathing gas close to the patient. It is further preferred that the mouthpiece is situated at (or close) to the end of the tube being close or proximate to the patient. Preferably, the mouthpiece is permanently or removably fixed to the tube and/or a part of the tube, preferably an integral part of the tube.

In one embodiment, the present invention provides a mouthpiece for controlled delivery of a breathing gas including oxygen, preferably an increased ratio of oxygen with respect to ambient air, to the respiratory tracts of a user. The mouthpiece comprises a valve having two modes; a closed default mode, which substantially impedes any flow of the breathing gas through the valve; and an active open mode, which allows for a substantial flow of the breathing gas through the valve, wherein the open mode can be activated by the user manipulating the valve with his/her mouth.

Preferably, the mouthpiece is substantially gas tight. Preferably, all portions of the mouthpiece except for an opening of the valve in the open mode are gas tight. That is, they are adapted to not allow the breathing gas to pass through. Preferably, the mouthpiece comprises (and more preferably consists of) materials being impermeable for the breathing gas. Thus, the entire mouthpiece including the valve is gas tight in the closed position of the valve.

In the context of the present invention, an increased ratio of oxygen in a gas with respect to ambient air generally refers to a ratio of oxygen being higher than 21%. However, it is preferred that the ratio is higher than 30%, preferably higher than 50%, more preferably higher than 70%, most preferably pure oxygen (i.e. up to 100% oxygen).

In the context of the present invention, substantial impedance of a flow refers to a flow being substantially less than the average flow in the open mode. Preferably, substantial impedance of a flow refers to a flow being less than 20% of the average flow in the open mode, more preferably less than 10% of the average flow in the open mode, most preferably less than 2% of the average flow in the open mode. In other words, if a flow at a given pressure, such as 20 cmH2O in the open mode of the valve is 100%, the flow at this pressure in the closed mode is less than 20%, preferably less than 10% and also preferred less than 2% of the flow in the open mode.

Furthermore and also in the context of the present invention, a default mode of a valve is understood as being a mode generally present when the user does not act in any way. In other words, it is the mode being present when the valve is "left alone" or relaxed. This is in contrast to an active mode. In the context of the invention, an active mode is characterized by the user interacting with the valve. Examples of this interaction may include, but are not limited to, applying pressure, sucking, breathing in, biting onto a designated area and the like.

The fact that the user can switch between a default closed mode and an active open mode leads to the breathing gas being released when the user needs it. In contrast to the current state of the art the breathing gas does not need to flow continuously, e.g. intermittent release, but only when needed. This leads to less gas being used whilst achieving the same effect and makes the current invention more efficient and effective than the current state of the art. The fact that the user can switch between the two modes by manipulating the mouthpiece with his/her mouth makes the usage of the device very simple and convenient for the user. Also, compliance is improved.

The open mode can be activated by the user manipulating the valve with his/her mouth by applying a force generally perpendicular to the flow of the breathing gas. Preferably, the user may activate the open mode of the valve by applying the force generally perpendicular to the flow of the breathing gas by his or her lips and/or teeth. Applying a force generally perpendicular to the flow of the breathing gas may further be accomplished by biting onto the mouthpiece and/or pressing the lips against the mouthpiece. Overall, applying a force generally perpendicular to the flow of breathing gas may be intuitive and may feel natural to the user. It may further require only little effort by the user. As the device may be used in hospital environments and/or in situations, wherein the user feels uncomfortable, it may be important to provide the user with a device making him feel more comfortable. Applying a force generally perpendicular may ultimately contribute to the usability and the user-friendliness of the device. It may also contribute to the compliance of the user.

It is further preferred that in the open mode, the flow of the breathing gas is equidirectional. A flow vector represents the flow of the breathing gas at any given cross-section perpendicular to a longitudinal axis of the mouthpiece. We understand the term equidirectional to mean that the flow vectors at any two given cross-sections form an angle being close to 0° and preferably between 0° and 90°, more preferably between 0° and 30° and particularly preferably between 0° and 20° and most preferably between 0° and 10°.

An equi-directional flow of the breathing gas within the mouthpiece may result in less turbulence of the flow of breathing gas. Further, the flow of gas may be smoother. This may result in less noise and more effective delivery of the breathing gas to a user. A reduction of noise may further contribute to a more comfortable feeling of the patient. This may ultimately also result in improved user compliance.

It is further preferred that during use the flow vector in the distal portion of the mouthpiece is substantially parallel to a vector connecting the distal end of the mouthpiece and the user's airway and/or uvula. More preferably, these two vectors form an angle of between 0° and 45° between each other, particularly preferred between 0° and 30°, further preferred between 0° and 20° and most preferred between 0° and 10°. In other words, it is preferred that the mouthpiece is adapted to direct the flow of breathable gas towards the user's airway during use.

The terms "distal" and "proximal" are used as meaning distal and proximal from the oxygen source. In other words, the term "distal" describes a portion which is, during use, closer to a user than another portion (the latter would be referred to as the proximal portion). As a mere example, a tube with two ends is considered. One end is adapted to be placed into a user's mouth, whilst the other is adapted to remain outside the user. In such a case, the former would be referred to as the distal end, whilst the latter would be referred to as the proximal end. If the distal end comprises two portions, one of which is adapted to be in contact with the user's mouth and the other is adapted to be in contact with the user's throat, the first would be referred to as the proximal portion and the latter would be referred to as the distal portion. In other words, the term distal describes a portion which is, during use, closer to the user's core than another portion.

By directing the breathable gas towards the user's airways, breathing may be simplified. In contrast to this, if the flow of gas was not directed towards the user's airways, the breathable gas may more easily escape the user's mouth through the opening formed between the user's lips. Further, if the flow of breathable gas was directed towards the user's lips and/or hard palate, it may make the user feel uncomfortable. Further, when the breathable gas is directed towards the user's airway and/or when the flow of gas is, in the open mode of the mouthpiece, equi-directional within the mouthpiece, this may result in a relatively fast and continuous flow of breathing gas out of the mouthpiece and into the user's mouth. This may be desirable to prevent a flow path from getting clogged and/or blocked. Clogging and/or blockage of the flow path may for instance occur due to saliva and/or remains of food in the user's mouth. Therefore, having a continuous and relatively strong flow of breathing gas may be desirable. This may be achieved by the equi-directional flow and/or the flow being directed towards the user's airway, since any turns within the gas passage may ease clogging and/or blockage.

Preferably, the breathing gas is a pressurized breathing gas, preferably with a pressure between 0 cmH2O and 60 cmH2O, more preferably with a pressure between 2 cmH2O and 40 cmH2O, most preferably with a pressure between 3 cmH2O and 25 cmH2O. This may for example facilitate the flow of the breathing gas to the user.

Furthermore, it is preferred that the closed mode impedes and/or suppresses gas flow up to a gas pressure of 30 cm H2O and/or that the closed mode substantially impedes and/or suppresses the gas flow in both directions through the valve. This may in fact be a great advantage compared to the existing systems in which the gas tube is continuously open, since there will be no substantial mixture of the exhaled "used" air of the patient with the breathing gas.

There are different ways to achieve the difference in the fluxes of the breathing gas in the open and in the closed mode. Preferably, the flux cross section is smaller in the closed default mode than in the active open mode.

Preferably, the valve can be opened and/or held in open mode by the user applying a force to the valve with at least part of his/her mouth. This might be particularly convenient, as the breathing gas preferably enters the mouth of the user. Therefore, it might be simple and convenient for the user to use his/her mouth to switch between the open and the closed mode.

It is preferred that the force required to open the valve is less than 14 N. By this, the user may be able to conveniently handle the mouthpiece. The possibility of manipulating the mouthpiece with a force smaller than 20 N might be of particular interest as the users (e.g. patients) making use of this mouthpiece might not be in perfect physical shape and might not have the strength to easily activate a device where a substantially greater force would be required.

Preferably, the force can be applied by at least part of the user's denture and/or lips and/or tongue. Again, this might be a very easy, simple and convenient mode of operation for the user.

Moreover, it is preferred that the user's manipulation of the mouthpiece with his/her mouth causes the cross sectional shape of the mouthpiece to be different from the shape in the closed default mode and thus activates the valve of the mouthpiece. This might be a mechanism being both efficient and leading to the desired effect on the one hand, but also being relatively easy (and therefore inexpensive) to manufacture.

Preferably, the valve in the mouthpiece comprises at least two separable membranes which are in contact in the closed mode and are at least partially separated in the open mode. Once more, this embodiment of the invention might achieve the desired results and might at the same time be simple and inexpensive to manufacture. The contact between the membranes may, e.g., be achieved by the membranes abutting and/or overlapping each other.

It is furthermore preferred that the membranes can be separated by the user applying a force generally orthogonal to the flow of breathing gas. Examples of applying this force include, but are not limited to biting onto the mouthpiece, squeezing or bending the mouthpiece between the tongue and at least part of the denture squeezing the mouthpiece between the lips, squeezing or bending the mouthpiece with at least one lip and the tongue and the like.

According to another preferred embodiment of the current invention the mouthpiece comprises at least part of a tube and two separable membranes having the shape of semi ellipses and/or semi circles.

The tube is preferably made of a material comprising Silicone and/or thermoplastic elastomer TPE. This material combination may lead to a good flexibility and/or is resistive against physical stress, including, but not limited to different temperature, pressure, humidity, acid and alkaline liquids (in particular saliva), gases (in particular breathing gas and/or oxygen), exposure to light and the like. Preferably, the cross section of the tube has a dimension of 15-40 mm, more preferably 20-30 mm, most preferably 21-25 mm. This may lead to a good combination of flow of breathing gas and/or convenience for the user. The length of the tube is preferably chosen in such a way that the connection between the supply of the breathing gas (e.g. an outlet device in a hospital and/or a gas bottle) can be easily achieved. Typical dimensions of this length range from 30 mm to 60 mm, preferably from 35 mm to 50 mm, most preferably from 40 mm to 45 mm Preferably, the cross section of the tube is circular and/or elliptical.

The membranes can for example be made of Silicone and/or TPE. The exact material combination should again lead to inertness against, particularly repeated application of, physical stresses as mentioned above. Preferably, the material is also substantially flexible to allow the membranes to easily switch between open and closed mode. The membranes are preferably removably and/or permanently fixed to the tube and/or they can be a part of the tube, preferably an integral part of the tube. This may allow a simple and inexpensive manufacturing process. Preferred shapes for the membranes include, but are not limited to, semi-spherical and/or semi-elliptical shapes.

Moreover, the current invention provides a use of a valve in a device for delivery of breathing gas including oxygen, preferably an increased ratio of oxygen with respect to air, to the respiratory tracts of a user, wherein the valve has two modes; a closed default mode, which substantially impedes any flow of the breathing gas through the valve; and an active open mode, which allows for a substantial flow of the breathing gas through the valve, wherein the open mode can be activated by the user manipulating the valve with his/her mouth. Again, the use of such a valve in a device for delivery of breathing gas has the mentioned advantages compared to the existing solutions mentioned above.

In a preferred embodiment, the valve is a part, preferably an integral part, of a mouthpiece comprising any of the characteristics mentioned above.

The current invention also provides an apparatus for controlled delivery of a breathing gas including oxygen, preferably an increased ratio of oxygen with respect to air, to the respiratory tracts of a user comprising: a supply of the breathing gas, preferably as a pressurized breathing gas; a mouthpiece according to any of the characteristics mentioned above and a tube connecting the device and the mouthpiece. It is again preferred that the mouthpiece is an integral part of the tube. This might allow for an easy and economical production of the mouthpiece.

Finally, the current invention also provides a method for controlled delivery of a breathing gas including oxygen, preferably an increased ratio of oxygen with respect to air, to the respiratory tracts of a user with the following steps: providing an apparatus comprising any of the features mentioned above and comprising a supply of the breathing gas, preferably pressurized breathing gas, a mouthpiece with any of the features mentioned above and a tube connecting the device and the mouthpiece; supplying the breathing gas, preferably as a pressurized breathing gas; activating the valve by applying a force generally orthogonal to the flow of the breathing gas and thereby generating a flow of the breathing gas; deactivating the valve by releasing the force and thereby substantially stopping the flow of the breathing gas.

Again, this method is more economical than the methods known in the prior state of the art, since the device does not release breathing gas permanently, but only when the user activates the mouthpiece. Preferably, the valve is activated by the user during inhalation and deactivated during exhalation.

The present invention is described by way of examples in more detail below referring to the following Figures, in which:

FIG. 3 shows another preferred embodiment of the present invention.

Figure 1A:
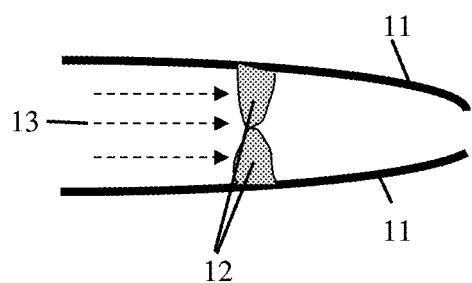
FIGS. 1a and 1b show top and cross sectional views of a preferred embodiment of a mouthpiece in the closed mode according to the present invention.
Figure 1B:
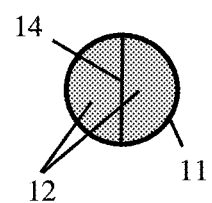

FIGS. 1a and 1b show a preferred embodiment of a mouthpiece in the closed mode according to the invention. In this embodiment, the mouthpiece is formed by the distal end of a tube and an integrated valve. FIG. 1a is a section through the tube and parallel to the designated flow direction of the breathing gas.

The Figure depicts the wall 11 of the tube, which is preferably made of a material comprising Silicone and/or TPE. This material combination may lead to a good flexibility and/or is resistive against physical stress, including, but not limited to different temperature, pressure, humidity, acid and alkaline liquids (in particular saliva), gases (in particular breathing gas and/or oxygen), exposure to light and the like. Furthermore, two membranes 12 are depicted, which form the valve in this example. These membranes can for example be made of Silicone and/or TPE. The exact material composition should lead to inertness against physical stresses as mentioned above.

Preferably, the membranes are adapted to enable a closed mode when they are in contact with each other (as depicted in FIG. 1a). In this mode, they resist a gas pressure, which is indicated by the dashed lines 13 and impede or even completely block flow of the gas, preferably flow of gas in both directions. The blocking mechanism can also be understood when considering the cross sectional perspective of FIG. 1b. Again, the wall 11 of the tube is depicted and also the two semicircles 12 of the membrane (which is one preferred embodiment of such a valve). As will be easily understood, the cross sectional view according to FIG. 1b is turned by 90° as compared to the cross sectional view according to FIG. 1a.

In the closed mode, it might be advantageous that the two membranes are in close, preferably direct contact with each other. This is indicated by the line 14. In fact, a contact might be desired in which there is no (e.g., cross sectional) opening in between the two membranes. In this case, the flow of (breathing) gas is substantially blocked by the valve. However, other situations shall also be encompassed in which the two membranes 12 do not completely abut each other but leave a small slot or opening which allows for a reduced and/or impeded flow of breathing gas. Preferably, this mode is the default mode of the valve—that is the mode being present when the user does not interact with the valve, i.e. the mode when the valve is "left alone". In other word, it is the relaxed mode of the valve.

Figure 2A:
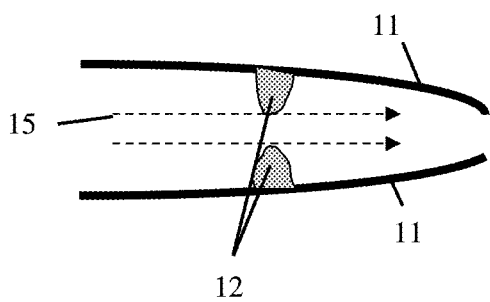
FIGS. 2a and 2b show top and cross sectional views of the mouthpiece of FIG. 1 in the open mode.
Figure 2B:
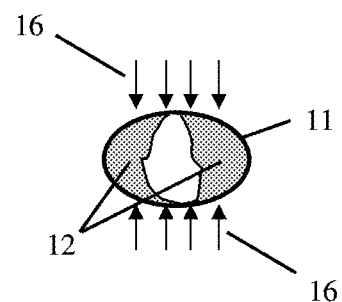

When considering the situation of the open mode, reference is made to FIGS. 2a and 2b. FIG. 2a is essentially a section from the same perspective as FIG. 1a. The only difference is the fact that the valve is now in open mode. A feature of this open mode of the shown embodiment is that the membranes 12 are no longer in substantial contact with each other, therefore now allowing a flow of gas as indicated by the dashed arrows 15. The cross sectional perspective of the tube and the membranes in open mode is depicted in FIG. 2b. As in FIG. 1b, the cross sectional view of FIG. 2b is turned by 90° as compared to FIG. 2a. Here, it is clearly visible that the membranes 12 are no longer in contact but that there is a free space in between them when viewed from the cross sectional perspective. The reason for this is a force that is applied in a direction generally orthogonal to the flow direction of the gas flow. The force acts on the valve in the area or plane of the membranes 12 and is indicated by the solid arrows 16. This force leads to a deformation of the tube 11 (in this example from a shape similar to a perfect circle to an ellipse-like shape when viewed in a cross sectional perspective) and causes the membranes to allow a free space in between them. Gas can then flow in the designated direction (usually towards the user).

FIG. 3 shows another embodiment of a mouthpiece in accordance with the present invention. Here, the mouthpiece corresponds to the one shown in and discussed with regard to the preceding Figs., e.g., FIG. 2a. Generally any mouthpiece in accordance with this invention may be used. In this embodiment, the mouthpiece 10 is attached to a breathing tube 20, such as a standard breathing tube, by means of an adapter 30. Adapter 30 preferably comprises a body 32, preferably made of a solid material such as polyethylene (PE), polypropylene (PP) and/or polycarbonate (PC) etc. The provision of a solid tube body 32, particular in combination with a soft mouthpiece 10 (soft as compared to the adapter 30 and/or body 32), may be of particular advantage. Firstly, the adapter may provide a defined interface to a, preferably standard, breathing tube. This may particularly allow connection of filters or other accessories. The solid structure of the body may also or alternatively make it easier to hold the mouthpiece.

According to a preferred embodiment, the body is provided with a connector means 36, preferably a bail, for attaching holding means, preferably a strap or the like. This may advantageously allow the patient to wear the mouthpiece always in a position close to the mouth even when it is not used. This is particularly useful if the mouthpiece is, for example, used with patients requiring a wheelchair.

Also, preferably, the body may be provided with or without a defined vent flow. The provision of a vent 34, preferably allowing a defined vent flow, may be of particular advantage. In particular, it may be easier to adapt the mouthpiece to NIV BiLevel devices, particularly without changing therapy parameters. Preferably, a vent has a flow in the range of about 30 l/min at 20 cmH2O.

It should be appreciated that the depicted embodiments are to be understood as examples and do not limit the present invention. For instance, in the depicted Figures, the mouthpiece is (an integral) part of a tube. However, it could also be a device attached to a tube, preferably permanently fixed and/or releasably connected. Instead of using a tube to connect the mouthpiece to a supply of breathing gas, other embodiments (which are not depicted) could for example comprise a direct connection of a breathing gas supply to the mouthpiece. Furthermore, the Figures depict a cross sectional shape of the tube which is essentially circular in the closed relaxed state and essentially elliptical in open state. Again, this is chosen as an example and does not limit the present invention. Other examples for possible shapes include, but are not limited to, shapes that are generally elliptical in both modes (open and closed), preferably changing their exact dimensions between the two states, and/or also cross sections which are essentially rectangular and the like. Furthermore, there are two membranes depicted. This is again just chosen by way of example—three or more membranes are also included in the scope of the present invention (as is one membrane with a designated slot which can open and close). By way of example, in the cross sectional view, the two membranes have a generally semi circular shape. Preferably, any other cross-sectional shape, including—but not limited to—shapes that are generally semi-elliptical and generally rectangular, can be chosen for the membranes. Moreover, the membranes are depicted in such a way that they close generally flush in the closed mode leading to a form-fit abutment of the membranes. That is the overlap of the two membranes is rather small. Again, other preferred alternatives include, but are not limited to, the membranes having a substantial overlap in the closed mode.

Finally, when viewed from the top, the membranes are depicted to be essentially perpendicular to the designated direction of flow of the breathing gas. This is again just one example of an embodiment of the present invention. Other preferred alternatives include, but are not limited to, the membranes "bending" into the tube when viewed from this direction. In other words, in the top perspective, it may be preferred that the membranes have a curvature, e.g. in order to stabilize the membrane against the gas pressure.

The invention claimed is:

1. A system for controlled delivery of a breathing gas to the respiratory tracts of a user, the system comprising:
   a pressurized breathing gas source adapted to deliver breathing gas with a pressure between 2 cmH2O and 40 cmH2O; and
   a mouthpiece configured to receive the breathing gas at the pressure, the mouthpiece comprising a valve having at least one deformable membrane and being operable in two modes;
      a default mode, in which the at least one deformable membrane at least partially impedes flow of the breathing gas through the valve; and
      an open mode, in which the at least one deformable membrane allows for flow of the breathing gas through the valve that is greater than any flow in the default mode, wherein the open mode is user-activatable by the user manipulating the valve with the user's mouth by applying a force substantially proximate the at least one deformable membrane of the valve and perpendicular to the flow of the breathing gas.

2. The system according to claim 1, wherein the default mode, the valve is structured to impede and/or suppress gas flow up to a gas pressure of 30 cmH2O.

3. The system according to claim 1, wherein the default mode substantially impedes and/or suppresses gas flow in both directions through the valve.

4. The system according to claim 1, wherein a cross section is smaller in the default mode than in the open mode.

5. The system according to claim 1, wherein the valve is structured to be opened and/or held in the open mode by the user applying a force to the valve with at least part of his/her mouth.

6. The system according to claim 1, wherein the force required to open the valve is less than 14 N.

7. The system according to claim 1, wherein the force can be applied by at least part of the user's denture and/or lips and/or tongue.

8. The system according to claim 1, wherein the user's manipulation of the mouthpiece with his/her mouth causes the cross sectional shape of the mouthpiece to be different from the shape in the default mode and thus activates the valve of the mouthpiece.

9. The system according to claim 1, wherein the valve comprises at least two separable membranes which
   are in contact in the default mode; and
   are at least partially separated in the open mode.

10. The system according to claim 9, wherein the membranes can be separated by the user applying a force generally orthogonal to a flow of the breathing gas.

11. The system according to claim 1, wherein the mouthpiece comprises at least part of a tube and two separable membranes having the shape of semi ellipses and/or semi circles.

12. The system according to claim 1, wherein the mouthpiece is attachable to and/or attached to an adapter.

13. The system according to claim 12, wherein the adapter is more rigid than the mouthpiece.

14. The system according to claim 1, which is adapted to provide a substantially equidirectional flow of breathing gas.

15. The system according to claim 1, wherein during use a flow vector in a distal portion of the mouthpiece is substantially parallel to a vector connecting a distal end of the mouthpiece and the user's airway and/or uvula.

16. The system according to claim 1, which is adapted to direct a flow of the breathing gas towards the user's airway during use.

17. The system according to claim 1, further comprising a tube connecting the pressurized breathing gas source and the mouthpiece.

18. The system according to claim 17, wherein the mouthpiece is an integral part of the tube.

19. The system according to claim 17, wherein the valve is an integral part of a mouthpiece.

20. The system according to claim 1, further comprising a vent provided upstream of the valve.

* * * * *